United States Patent [19]

McGarrity et al.

[11] 4,387,161

[45] Jun. 7, 1983

[54] DETECTION OF MYCOPLASMA INFECTION IN CELL CULTURES

[75] Inventors: Gerard J. McGarrity, Wenonah, N.J.; Dennis A. Carson, Del Mar, Calif.

[73] Assignee: Institute for Medical Research, Camden, N.J.

[21] Appl. No.: 283,934

[22] Filed: Jul. 16, 1981

[51] Int. Cl.³ .................... C12Q 1/04; C12Q 1/22; C12N 5/00; C12R 1/35

[52] U.S. Cl. ........................ 435/34; 435/31; 435/240; 435/870

[58] Field of Search ............ 435/29, 31, 32, 33, 435/34, 240, 241, 870

[56] References Cited

U.S. PATENT DOCUMENTS 3,668,075  6/1972  Cekoric, Jr. et al. ............ 435/870 X

OTHER PUBLICATIONS

Aaron Bendich et al., Ciba Foundation Symposium on the Chemistry and Biology of Purines; Little Brown & Co., pp. 18, 19, 75 and 76; 1957.

Masakazu Hatanka et al., Proc. Nat. Acad. Sci., USA, vol. 72, No. 4, pp. 1401–1405; 1975.

Gerard J. McGarrity et al., In Vitro, vol. 15, No. 2, pp. 73–81; 1979.

Gerard J. McGarrity et al., Experimental Cell Research, vol. 121, pp. 159–165; 1979.

S. Senesi et al., FEBS Letters, vol. 64, No. 2, pp. 353–357; 1976.

T. P. Zimmerman et al., Canadian Journal of Biochemistry, vol. 49, pp. 1050–1054; 1971.

Chemical Abstracts, vol. 95, 198115u; 1981.

In Vitro, vol. 12, pp. 643–648, (1977) by McGarrity.

In Vitro, vol. 9, pp. 17–18, (1973) by McGarrity.

Methods in Enzymology, vol. 58, pp. 18–29, (1978) by McGarrity.

Selective Killing of Leishmania Infected Mouse Macrophages by 6-Methypurine 2′-Deoxyriboside, by Carson & Chang, Life Sciences vol. 29, pp. 1617–1621.

Primary Examiner—Robert J. Warden

Attorney, Agent, or Firm—Schuyler, Banner, Birch, McKie & Beckett

[57] ABSTRACT

Detection of mycoplasma infection in an animal cell culture is accomplished by growing animal cells from a culture in a growth medium in the presence of 6-methylpurine deoxyriboside and determining whether animal cells are killed.

6 Claims, No Drawings

DETECTION OF MYCOPLASMA INFECTION IN CELL CULTURES

Mycoplasma infection is a particularly insidious problem which attends the maintenance and use of cell cultures. As a threshold matter there has been no easy technique for the reliable detection of mycoplasmas in a cell culture. Mycoplasmal infection may not kill cells or stop them from reproducing, yet mycoplasmas have their own metabolic activity and can potentially affect many cell culture parameters. The detection of mycoplasmal infection in a cell culture, therefore, can cloud or invalidate experimental procedures carried out utilizing that cell culture. While cells, as supplied, may contain undetected mycoplasmas, mycoplasma-free cell cultures can also become infected by mycoplasmas during laboratory use. Such infection apparently can occur from other cell cultures infected with mycoplasmas, from nutrient media or from cell culture personnel. Assays of mammalian cell cultures in one laboratory over a period of several years resulted in an annual detection rate of mycoplasmal infection ranging from 3% to 15%. Such results demonstrate that mycoplasma contamination of cell cultures is a significant problem.

Many techniques have been advanced for the detection of mycoplasmal infection in cell cultures. These techniques include, inter alia, microbiological aerobic and anaerobic incubation, immunofluorescence, DNA staining, scanning electron microscopy, and biochemical procedures. (See, e.g., *Experimental Cell Research*, 121 (1979) 159-165). Such procedures vary in their overall efficiency but all require very close quality control and often require specialized techniques or expensive equipment. There is a need for an easy, efficient and economical assay to determine if cells are infected by mycoplasma.

It is an object of this invention to provide a method for the detection of mycoplasmal infection of cell cultures which is economical and efficient.

In accordance with this invention, it has been determined that mycoplasmas convert non-toxic 6-methylpurine deoxyriboside into 6-methylpurine and/or 6-methylpurine riboside, each of which is selectively toxic to animal cells and which will selectively kill animal cells in a culture. Accordingly, this invention is directed to a method of detecting mycoplasma infection in an animal cell culture which comprises growing animal cells from such culture in a growth medium in the presence of 6-methylpurine deoxyriboside and determining whether animal cells are killed.

The term mycoplasmas is a conventional term used in the art to refer to microorganisms of the family Mycoplasmataceae. Such family includes, for example, microorganisms or parasites of the genus Mycoplasma, the genus Acholeplasma, and the genus Spiroplasma.

Mycoplasmas, in general, exhibit sufficient adenosine phosphorylase activity to convert non-toxic 6-methylpurine deoxyriboside (sometimes referred to herein as 6-MPDR) to 6-methylpurine or 6-methylpurine riboside which are toxic to cells. While animal cells themselves may exhibit some adenosine phosphorylase activity, the level of activity is low and does not adversely affect the growth of cells, even when 6-methylpurine deoxyriboside is present in the medium. Importantly, the method of this invention does not require expensive equipment or sophisticated and unusual techniques. It may be carried out employing standard laboratory cell culture techniques in readily available equipment. It is economic and provides good reliability for the determination of mycoplasma contamination of cell cultures.

This invention is applicable generally to animal cells including cultures of mammalian cells, reptillian cells, piscan cells, avian cells, amphibian cells and insect cells. Mammalian cell in vitro cultures are of particular importance in research and constitute an important area of application for the assay of this invention.

The assay of this invention can be carried out by incubating a specimen of the test cell culture in a medium that contains 6-methylpurine deoxyriboside and determining whether cells in the test culture are killed. Alternatively, and more preferably, an indicator cell culture can be employed to obtain more uniform results. In such event, the test cell culture is added to a medium which contains the indicator culture cells and the culture is monitored to determine if indicator cells are killed. While it is not absolutely essential, it is preferred to conduct replicates and to conduct controls in which the test cell culture is grown in a medium that does not contain 6-methylpurine deoxyriboside.

The cell media and growth conditions employed in this invention may be any of those known in the art. A typical growth medium for mammalian cells contains 10% fetal bovine serum and is characterized by a pH of about 7.2. Incubation or growth of such cells is generally carried out at a temperature from about 36° to about 38° C. and most often at about 37° C. under an atmosphere that contains $CO_2$. Typically an air atmosphere containing 5% $CO_2$ is employed, although a $CO_2$ buffer in the media can also be utilized. The choice of a particular growth medium and particular incubation conditions for each category of cells may vary but is readily within the skill of the art.

The 6-methylpurine deoxyriboside is known and may be prepared employing techniques known in the art. In one such technique, 6-methylpurine deoxyriboside may be prepared from 6-methylpurine employing a trans-deoxyribosylase obtained, for example, from *Lactobacillus helveticus* (ATTC 8018). See, e.g., *Proc. Nat'l. Acad. Sci. USA*, 77, 1980 (6865). The adenosine phosphorylase (adenosine:orthophosphate ribosyltransferase) of the mycoplasmas converts 6-methylpurine deoxyriboside to both 6-methylpurine and to 6-methylpurine riboside in the presence of phosphate in the nutrient medium. Standard nutrient media contain adequate phosphate for this assay but, of course, additional phosphate, such as a soluble inorganic phosphate, can be incorporated into the medium if desired.

The concentration of 6-methylpurine deoxyriboside to be added to the test media is in large measure a matter of choice. Generally concentrations within the range of from about 5 to about 40 micromoles (and often a concentration of about 10 micromoles) have been used satisfactorily in tests. Even some toxicity was observed at concentrations as low as 1 micromole of 6-methylpurine deoxyriboside. In order to avoid possibly ambiguous results, however, it is preferred to employ a concentration of at least about 5 micromoles. While concentrations above about 40 micromoles can be employed, such concentrations add unnecessarily to the expense of the assay. The 6-methylpurine deoxyriboside can be present in the medium from the outset or can be added at intermediate stages as described below.

In carrying out the assay of this invention, it is desirable to incubate the test culture for a period of time (for example, 2-4 days) so that any mycoplasma can achieve a reasonable concentration before the 6-methylpurine deoxyriboside is added to the growth medium. After the 6-methylpurine deoxyriboside is added to the medium, the test cells are observed periodically employing standard art techniques to determine destruction of cells. Cell destruction can be determined by simple visual inspection of the cell monolayer. If desired, cell destruction can be quantified by counting the number of cells per unit area and comparing that result with the number of cells obtained in the same area of a control test which does not contain 6-methylpurine deoxyriboside. The cell destruction which occurs in infected cultures when the assay of this invention is employed is generally substantial. Cell destruction of 50% or even 90% are often obtained after only a few days. Generally, it is preferred that the culture be carried out for at least about 3 days before it is concluded that no mycoplasma infection exists.

The number of cells in a test sample or inoculum is also a matter of choice and is readily within the skill of the art. The smaller the inoculum, the longer it generally will take to obtain meaningful cell growth. Generally, test specimens have not been subjected to cell counts. Rather a flask having a 25 cm$^2$ surface has been inoculated with about 0.1 ml of a 3 or 4 day old test culture. Both media and cells have generally been added to the assay media although only the cells can be employed if desired. When an indicator cell culture is used, an inoculum of about $1 \times 10^4$ cells per cm$^2$ of growth area has been employed. These procedures are merely representative and can vary widely.

In a typical procedure employing the test cell culture itself, a specimen of the test culture is inoculated into a standard growth medium and is grown for about three days. Thereafter, 10 micromoles of 6-methylpurine deoxyriboside is added to the medium and the incubation is continued with observation made daily to determine if cells of the test culture are being destroyed. Desirably, a control is also conducted in which the above steps are repeated except that 6-methylpurine deoxyriboside is not added to the medium. In accordance with normal biological procedures, it is desirable to conduct at lest one replicate for both the test procedure and the control.

When an indicator cell culture is employed in the assay of this invention, that cell culture is desirably first inoculated into the growth medium and allowed to grow. Thereafter, for example a day later, the medium may be inoculated with a specimen of the test cell culture and incubation is conducted for another period of time (e.g., 3-4 days) to permit growth of the mycoplasmas. Then 6-methylpurine deoxyriboside is added to the medium and the culture is observed periodically for toxicity. Once again controls and replicates are desirably run.

If an indicator cell culture is employed, it may prove desirable to check the parent indicator cell culture from time to time to insure that it has not become contaminated with mycoplasma. This may be done by culturing a test specimen of the indicator cells in normal culture medium, and culturing another test specimen of the cell in a growth medium that contains 6-methylpurine deoxyriboside. In addition, if desired, indicator parent cells may be cultured in a growth medium to which mycoplasma have been added and, in addition, cultured in a growth medium in which both mycoplasma and 6-methylpurine deoxyriboside have been added.

The choice of an indicator cell culture is readily within the skill of the art. In tests reported herein to mycoplasma-free 3T6 mammalian cells (mouse embryo cell fibroblast) were employed. These are readily available cells widely used in research and are referred to, inter alia, in *Experimental Cell Research*, 121 (1979) 159-165. Other mycoplasma-free animal cells may, of course, be used as indicator cells as may cells of bacteria which do not exhibit adenosine phosphorylase and to which 6-methylpurine and/or 6-methylpurine ribose are toxic. Species of Lactobacillus may, for example, be used. The use of indicator cells is primarily to provide a more uniform result by minimizing the differences in toxic response to 6-methylpurine or 6-methylpurine riboside which may occur from one type cell to another type cell. As noted earlier, the use of indicator cells, while preferred, is not required for the practice of this invention.

While reference is made to a control, it is not essential that the control be conducted concurrently with the test specimen. The growth of any given cell line can be determined in a medium that does not contain 6-methylpurine deoxyriboside and that result can be utilized as a standard. If test or indicator cells which have a toxic response to 6-methylpurine or 6-methylpurine riboside are not destroyed in a medium that contains 6-methylpurine deoxyriboside, it can be concluded that the test specimen does not contain mycoplasma and no controls are required. If cells are destroyed, then controls are recommended to insure that the observed toxic response is due to mycoplasma infection of the test culture.

The following examples are included for illustrative purposes only and are not intended to limit the scope of this invention.

In the following examples, 6-methylpurine deoxyriboside was prepared from 6-methylpurine (Sigma, St. Louis) using a transdeoxyribosylase from *Lactobacillus helveticus* (ATCC 8018) and thymidine as the deoxyribose donor by a modification of the method of Cardinaud. Such modified method is described in *Proc. Nat'l. Acad. Sci. USA*, 77 (1980) 6865. The product was purified by chromatography on AG1-X8 (Biorad, Richmond, CA) in 20% acetonitrile, 10 mM KPO$_4$ (pH 6.0). The nucleoside was 97% pure when analyzed by reverse phase high performance liquid chromatography (HPLC), and yielded a single ultraviolet absorbing spot after thin layer chromatography on cellulose plates developed either in the acetonitrile based solvent system described above, in 1 M ammonium acetate.

EXAMPLE I

Cell cultures assayed included a series of human fibroblasts and lymphocytes submitted to the Institute for Medical Research Camden, New Jersey, for cell banking but rejected because of mycoplasmal infection. (Mycoplasmal assays employed to detect the infection were microbiological culture, DNA staining and specific immunofluorescence.) Ampules of frozen cells, $5 \times 10^5$ cells/ampule, were removed from liquid nitrogen, quickly thawed and inoculated into a T25 flask (Falscon Plastics) with Hams F-12 medium and 10% inactivated fetal bovine serum. Flasks were incubated at 37° C. in 5% CO$_2$ in air. After 3-4 days incubation, 10 uM 6-methylpurine deoxyriboside was added in a volume of 0.1 ml. Cultures were observed daily for signs of cytopathology. Controls consisted of infected cultures without 6-methylpurine deoxyriboside and mycoplasma free cultures treated with 6-methylpurine deoxyriboside.

These cultures consisted of fibroblasts and lymphocytes and included human, mouse, monkey and mouse-human hybrids. The results are shown in Table 1.

TABLE 1

| Cultures Infected with: | No. Positive[2]/No. Tests |
|---|---|
| M. hyorhinis | 40/42 |
| M. orale | 8/9 |
| A. laidlawii | 23/23 |
| M. arginini | 3/3 |
| M. salivarium | 7/7 |
| M. orale and M. pneumoniae | 4/4 |
| M. sp. 70-159 | 2/2 |
| TOTALS | 87/90 |

[2] Judged by at least 50% cytopathic effect.

The 6-methylpurine deoxyriboside detected mycoplasma infection in 87 of 90 cultures (96.6%). The three cultures that were not detected were: 2 human fibroblasts infected with M. hyorhinis, and a mouse tumor line infected with M. orale. In the two cases of M. hyorhinis infection, the cultures grew slowly after removal from liquid nitrogen with and without 6-methylpurine deoxyriboside and this may have accounted for the indication of no apparent toxicity. In the other false negative, toxicity was also apparent in the control without 6-methylpurine deoxyriboside apparently due to mycoplasmal infection. The three cultures that yielded false negatives or questionable results in these tests, however, were detected when tested in the tests reported in Example II below.

The cytopathic effect was easily discernible in infected cultures after 6-methylpurine deoxyriboside additions, resulting in destruction of at least 50% and usually 90-100% of the monolayers. Lymphocyte cultures were judged by cell counts.

EXAMPLE II

In addition to the studies of Example I, specimen cell cultures were inoculated into a 3T6 embryo fibroblast indicator culture. (Indicator cultures of 3T6 have been used as an adjunct in DNA staining and immunofluorescent assays as reported in In Vitro, 15 (1979) 73.) The test cell culture specimens were harvested 3-4 days after passage and included cells and spent medium.

Coverslips were inoculated with $1.5 \times 10^4$ 3T6 cells and grown in minimal Eagles medium (MEM)+10% fetal bovine serum for 24 hours at 37° C. in 5% $CO_2$-air at which time the specimen cell culture was added in a volume of 0.1 ml. The culture was incubated an additional 2-3 days at which time 6-methylpurine deoxyriboside was added in a final concentration of 10 uM. Negative controls consisted of uninoculated 3T6 cells and inoculated 3T6 containing 10 uM 6-methylpurine deoxyriboside. Positive controls consisted of mycoplasma (M. hyorhinis) infected 3T6 cells, with and without 6-methylpurine deoxyriboside. The results are shown in Table 2.

TABLE 2

| Inocula Into 3T6 Specimen Cultures Infected with: | No. Positive/No. Tested |
|---|---|
| M. hyorhinis | 9/9 |
| M. orale | 3/3 |
| A. laidlawii | 8/8 |
| M. salivarium | 2/2 |
| M. arginini | 3/3 |
| M. sp 70-159 | 2/2 |

TABLE 2-continued

| Inocula Into 3T6 Specimen Cultures Infected with: | No. Positive/No. Tested |
|---|---|
| M. orale +M. pneumoniae | 2/2 |
| TOTALS | 28/28 |

As demonstrated, the indicator system correctly identified all 28 specimens as being infected.

EXAMPLE III

In other studies, 3T6 cultures were deliberately infected with various mycoplasma species. Approximately $1 \times 10^5$ colony forming units (CFU) were added to 3T6 cultures. Cultures were incubated and passaged a minimum of two weeks before addition of 6-methylpurine deoxyriboside. The following mycoplasma strains were studied: M. hyorhinis GDL (ATTC 23839); M. orale JS (ATCC 29802); M. arginini VA (ATCC 29801); M. salivarium VV (ATCC 29803); A. laidlawii MG (ATCC 29804); M. pneumoniae FH (ATCC 15531); M. fermentans; and M. hominis. The M. fermentans and M. hominis strains used in this study were isolated from cell cultures. The results are shown in Table 3.

TABLE 3

| Culture | Culture Toxicity[1] |
|---|---|
| 3T6 (no 6 MPDR) | — |
| 3T6 | — |
| 3T6+ M. hyorhinis | + |
| 3T6+ M. orale | + |
| 3T6+ M. arginini | + |
| 3T6+ M. salivarium | + |
| 3T6+ A. laidlawii | + |
| 3T6+ M. hominis | + |
| 3T6+ M. fermentans | + |
| 3T6+ M. sp. 70-159 | + |
| 3T6+ M. buccale | + |

[1] Minimum of 50% CPE

EXAMPLE IV

To determine the effect of 6-methylpurine deoxyriboside on mycoplasma-free cultures, 10 uM 6-methylpurine deoxyriboside was added to various types of 3-day old cultures which were thereafter maintained for an additional 3-4 days. The effects are presented in Table 4. No toxicity was apparent in any of the 10 cultures tested.

TABLE 4

| Cell Culture | | Toxicity |
|---|---|---|
| 3T-6 (mouse) | | — |
| IMR-90 (human) | | — |
| MDCK (canine) | | — |
| Vero (monkey) | | — |
| African Green Monkey Kidney | | |
| AG-2410[1] | (smooth muscle) | — |
| AG-2411 | (smooth muscle) | — |
| AG-2791 | (endothelial) | — |
| AG-3905 | (endothelial) | — |
| GM-1056 | (human lymphocyte) | — |

[1] Accession numbers of Institute of Medical Research, Camden, N.J.

EXAMPLE V

While culture toxicity and cytopathic effect can be somewhat subjective observations, the level of 6-methylpurine deoxyriboside toxicity in tests made according to this invention has been readily discernible and yielded at least 50% destruction of the cell sheet. In most cases, there was 0-10% confluency of mycoplasmal infected cultures in the presence of 6-methylpurine deoxyriboside, 90-100% confluency of mycoplasmal free cultures, both with and without 6-methylpurine deoxyriboside. In infected cultures that showed complete destruction of the culture in the presence of 6-methylpurine deoxyriboside, no viable cells could be detected with trypan blue staining. To quantitate the number of cells with cytopathic effect (CPE), viable counts were performed on 3T6 indicators inoculated with different infected cultures. Results are presented in Table 5. Even cultures that show 50% cytopathic effect have approximately a 3 log reduction in viable cells by trypan blue.

TABLE 5

| Culture | % CPE | No. Viable Cells/ 25 cm² flask |
|---|---|---|
| 3T6 | 0 | $3.0 \times 10^6$ |
| 3T6 + #1000[1] | 0 | $1.8 \times 10^6$ |
| 3T6 + #1000 + 6MPDR | 50 | $2.0 \times 10^3$ |
| 3T6 + M. arginini | 0 | $4.010^6$ |
| 3T6 + M. arginini + 6MPDR | 100 | 0 |

[1]Culture infected with M. hyorhinis

EXAMPLE VI

Cultures of A. laidlawii and M. hyorhinis were grown in the presence and absence of 10 uM 6-methylpurine deoxyriboside. Growth curves of the treated and untreated cultures were identical which demonstrates that the 6-methylpurine deoxyriboside was not toxic to the mycoplasmas. Lack of toxicity was also indirectly demonstrated by the fact that viable mycoplasmas were always obtained from infected cell cultures treated with 6-methylpurine deoxyriboside.

EXAMPLE VII

To determine if 6-methylpurine deoxyriboside was toxic for 3T6 cells, dose response studies were performed. 6-methylpurine deoxyriboside had no discernible effect on 3T6 even at concentrations of 40 micromoles. With 6-methylpurine, however, some cytopathic effect was observed at concentrations as low as 1 uM. No viable cells were detected at 6-methylpurine concentrations of 10, 20 and 40 micromoles. Similar results were obtained with 6-methylpurine riboside.

Since modifications of this invention will be apparent to those skilled in the art it is intended that this invention be limited only by the scope of the appended claims.

We claim:

1. A method of detecting mycoplasma infection in an animal cell culture which comprises growing a specimen of animal cells from such culture in a growth medium in the presence of 6-methylpurine deoxyriboside and determining whether animal cells are killed.

2. The method according to claim 1 wherein animal cells are grown in a culture medium for an initial period of time and 6-methylpurine deoxyriboside is thereafter added to the medium.

3. The method according to claim 1 wherein
   (a) mycoplasma-free indicator cells are incubated in a growth medium and a specimen of test cells is added to the growth medium and further incubation is effected, said medium containing 6-methylpurine deoxyriboside during at least the later portions of incubation; and
   (b) the culture is monitored to determine if indicator cells are killed.

4. The method according to claim 1 wherein
   (a) mycoplasma-free indicator cells are incubated in a growth medium;
   (b) a specimen of test cells is added to the growth medium and further incubation is effected;
   (c) 6-methylpurine deoxyriboside is added to the growth medium and still further incubation is effected; and
   (d) the culture is monitored to determine if indicator cells are destroyed.

5. The method according to claim 1 wherein the animal cell culture is a mammilian cell culture.

6. The method according to claim 1 wherein at least about 5 micromoles of 6-methylpurine deoxyriboside is present in the growth medium.

* * * * *

UNITED STATES PATENT AND TRADEMARK OFFICE
CERTIFICATE OF CORRECTION

PATENT NO. : 4,387,161

DATED : June 7, 1983

INVENTOR(S) : Gerard J. McGarrity and Dennis A. Carson

It is certified that error appears in the above-identified patent and that said Letters Patent is hereby corrected as shown below:

Insert the following paragraph at column 1, line 4, before the heading:

"This invention was made with government support under Grant Numbers GM 23200 and AI 15748 awarded by the National Institutes of Health. The government has certain rights in the invention."

Signed and Sealed this

Tenth Day of May, 1994

Attest:

BRUCE LEHMAN

Attesting Officer

Commissioner of Patents and Trademarks